United States Patent [19]

Satake et al.

[11] Patent Number: 4,911,914

[45] Date of Patent: Mar. 27, 1990

[54] METHOD FOR PRODUCING AN EXHAUST GAS SENSOR

[76] Inventors: Kazuko Satake, 971-2, Imazyuku-Higashicho, Asahiku, Yokohama; Mariko Hanada, 3-4-11, Hatada, Oujicho, Kitakatsuragi, Nara; Kazuo Okino, 1-23-9, Tsukaguchicho, Amagasaki; Kazunari Komatsu, 3-7-11, Kaminukushina, Higashi-ku, Hiroshima-shi, all of Japan

[21] Appl. No.: 101,762

[22] Filed: Sep. 28, 1987

[30] Foreign Application Priority Data

Sep. 29, 1986 [JP] Japan ................................ 61-230288

[51] Int. Cl.$^4$ .................................................. C01G 19/00
[52] U.S. Cl. .................................. 423/593; 73/863; 324/71.5; 324/425; 324/694; 422/98
[58] Field of Search ......................... 423/593; 73/863; 422/98; 324/65 R, 71.5, 425

[56] References Cited

U.S. PATENT DOCUMENTS 2,413,762  1/1947  Gutzeit et al. ..................... 423/593
4,291,009  9/1981  Franks ............................... 423/593

FOREIGN PATENT DOCUMENTS 156915   9/1984  Japan ................................ 423/593
156916   9/1984  Japan ................................ 423/593
174527  10/1984  Japan ................................ 423/593
174528  10/1984  Japan ................................ 423/593
 71525   4/1985  Japan ................................ 423/593
161338   8/1985  Japan ................................ 423/593
61-155947  7/1986  Japan .

OTHER PUBLICATIONS

B. L. Chamberland and S. Silverman, "The Preparation and Characterization of Several Mixed Metal Hydroxides of the Type AB(OH)$_6$", *Journal of the Less-Common Metals*, 65, No. 2 (Jun., 1979), pp. 41–48.

*Primary Examiner*—John Doll
*Assistant Examiner*—Wayne A. Langel

[57] ABSTRACT

A method of producing an exhaust gas sensor incorporating BaSnO$_3$. Stannate ion and barium ion are reacted in a strong alkali to precipitate water-containing crystals of BaSnO$_3$ such as BaSnO$_3$.3H$_2$O, BaSnO$_3$.5H$_2$O or the like. When thermally decomposed, the precipitate gives BaSnO$_3$ free from segregated Ba and Sn elements. The product was then molded and thereafter sintered to obtain the sensor.

9 Claims, 11 Drawing Sheets

X300  X1000

METHOD FOR PRODUCING AN EXHAUST GAS SENSOR

FIELD OF THE INVENTION

The present invention relates to a method of producing an exhaust gas sensor having BaSnO$_3$ incorporated therein. The exhaust gas sensor of the invention is useful, for example, for detecting the air-fuel ratio of motor vehicle engines, boilers, heaters, etc.

PRIOR ART

We proposed an exhaust gas sensor incorporating BaSnO$_3$ (Unexamined Japanese Patent Publication SHO 60-205,342 corresponding to U.S. patent application Ser. No. 711,154 and to European Laid-Open Patent Application 0157,328). We also proposed to add a small amount of SiO$_2$ to BaSnO$_3$ to obtain increased oxygen sensitivity (Unexamined Japanese Patent Publication SHO 61-147,146 corresponding to U.S. Pat. No. 4,658,632 and to West German Laid-Open Patent Application 3545,372). We further found that BaSnO$_3$ causes corrosion to Pt electrodes in a reducing atmosphere at a high temperature and proposed to inhibit the corrosion of the Pt electrode by adding a small amount of ZrO$_2$ thereto (Unexamined Japanese Patent Publication SHO 62-14,047 corresponding to U.S. patent application Ser. No. 883,130).

In these proposals, we reacted BaCO$_3$ with SnO$_2$ at about 1200° to about 1400° C. to obtain BaSnO$_3$. We subjected the BaSnO$_3$ to X-ray diffraction, which revealed that the compount is in the form of almost perfect crystals. Electron photomicrographs of the product obtained showed that it is in the form of crystals having a distinct cystal plane (see Unexamined Japanese Patent Publication SHO 60-205,342).

The product BaSnO$_3$ was nevertheless found to contain trace segregation of Ba and Sn elements. The segregation involved is very slight and almost undetectable by X-ray diffraction or electron photomicrographs. The segregation is responsible for the decomposition of BaSnO$_3$ in exhaust gases, impairing the characteristics of the sensor. When free of segregation, BaSnO$_3$ exhibits improved oxygen sensitivity.

Aside from the above proposals or findings, David E. Williams et al. disclose in their British Laid-Open Patent Application No. 2,149,121 BaSnO$_3$ prepared by reacting BaCO$_3$ with SnO$_2$ at 700° to 1300° C. for about 16 hours. The resulting BaSnO$_3$ is used as a material for gas sensors. They disclose that pulverization and baking, when repeated several times as required, afford more completely reacted BaSnO$_3$.

Our experiments demonstrated that the starting materials of BaCO$_3$ and SnO$_2$, when repeatedly subjected to pulverization and baking, gave BaSnO$_3$ free of segregation. For example, when the mixture was baked at 1300° C. for 2 hours four times with an intervening pulverizing step between the successive baking steps, segregation-free BaSnO$_3$ was obtained, which was durable and exhibited high oxygen sensitivity during actual use.

However, many repetitions of pulverization and baking are disadvantageous in practice. Moreover, repeated pulverization and baking are likely to permit the contamination of BaSnO$_3$ during the treatment.

SUMMARY OF THE INVENTION

An object of the present invention is to provide a novel method of producing an exhaust gas sensor of the BaSnO$_3$ type. More specifically, an object of the invention is to make it possible to produce an exhaust gas sensor having increased durability and higher oxygen sensitivity for actual use. These objects can be fulfilled by eliminating the segregation of elements in BaSnO$_3$. Another object of the invention is to facilitate the production of segregation-free BaSnO$_3$, to obviate the need for a complex process including repeated pulverization and baking and to prevent the contamination of BaSnO$_3$ in this process. Still another object of the invention is to provide BaSnO$_3$ which is easy to mold.

According to the present invention, water-containing crystals of BaSnO$_3$ are thermally decomposed into BaSnO$_3$. The water-containing crystals of BaSnO$_3$ primarily include three hydrates: BaSnO$_3$.3H$_2$O, BaSnO$_3$.5H$_2$O and BaSnO$_3$.7H$_2$O. Further these crystals of BaSnO$_3$ include flaky crystals the water content of which is not determinable and which are produced transitionally during conversion from BaSnO$_3$.7H$_2$O to BaSnO$_3$.5H$_2$O. Thermogravimetric analysis reveals that these flaky crystals are similar to BaSnO$_3$.5H$_2$O in composition. Although it is not clear whether there are water-containing crystals other than those mentioned above, such other crystals, if available, are also usable.

Water-containing crystals of BaSnO$_3$ separate out, for example, when a Ba compound is reacted with a stannic acid solution stabilized with a strong alkali. The product, i.e. the precipitate, is in the form of acicular, flaky or like large crystals, which, when thermally decomposed, give BaSnO$_3$ free from segregated elements. The segregation of Ba or Sn element occurs in BaSnO$_3$ crystals because these ions are slow to diffuse in the baking step. For example, a mixture of BaCO$_3$ and SnO$_2$, when baked, provides BaSnO$_3$ crystals containing segregated Ba and Sn elements since these elements do not fully diffuse during the formation of BaSnO$_3$ To obviate the segregation, the BaSnO$_3$ must be repeatedly pulverized and baked. In contrast, water-containing crystals of BaSnO$_3$, when thermally decomposed, readily afford BaSnO$_3$ free of segregation since Ba ions and Sn ions are uniformly distributed from the beginning.

The characteristics of exhaust gas sensors incorporating BaSnO$_3$ are dependent on whether the compound is free of segregation. When involving no segregation, the compound exhibts improved durability and increased oxygen sensitivity in actual use. In respect of these characteristics, the segregation-free product resulting from the thermal decomposition of water-containing crystals of BaSnO$_3$ is comparable to the product obtained by reacting BaCO$_3$ with SnO$_3$ and subjecting the resulting BaSnO$_3$ to repeated pulverization and baking to eliminate segregation. However, the repetition of pulverization and baking of BaSnO$_3$ lowers the productivity of exhaust gas sensors and renders the BaSnO$_3$ susceptible to contamination during the pulverization and baking steps.

Water-containing crystals of BaSnO$_3$ precipitate as large acicular, flaky or like crystals and retain this form even after thermal decomposition. Accordingly, the BaSnO$_3$ prepared from water-containing crystals thereof is easier to mold than the usual particulate BaSnO$_3$.

EXAMPLE

Water-containing crystals of $BaSnO_3$

An aqueous solution of sannic acid (at least 13 in pH) stabilized with sodium hydroxide was reacted with an aqueous solution of barium chloride to obtain water-containing crystals of $BaSnO_3$ as a precipitate. The solvent may be an aqueous solvent chiefly comprising water. Besides water, also usable are water-methanol, water-ammonia, etc. The pH may be in such a range that will not permit precipitation of stannic acid. Instead of sodium hydroxide, potassium hydroxide, strong organic bases such as tetraethylammonium, etc. are usable for adjusting the pH. While the stannic acid solution used had a pH of 13, it was possible to prepare water-containing crystals even at a pH of 12, for example, when the stannic acid concentration was 0.005 mol/l. The stannate ion reacts with the barium ion, causing precipitation of water-containing crystals of barium stannate. The resulting crystals contain at least three kinds of hydrates, i.e., $BaSnO_3.7H_2O$ (stable at temperatures of up to 50° C.), $BaSnO_3.5H_2O$ (stable at 50° to 60° C.) and $BaSnO_3.3H_2O$ (stable at temperatures of at least 65° C.). In addition to these hydrates, the conversion of $BaSnO_3.7H_2O$ to $BaSnO_3.5H_2O$ was likely to involve formation of flaky crystals of a composition (the water content determined by thermogravimetric analysis) similar to $BaSnO_3.5H_2O$. Depending on the conditions involved, these compounds precipitate in the form of a mixture. The reaction product has yet to be checked for the presence or absence of other hydrates. The hydrates separating out were colorless, transparent, and acicular or flaky in form. In the size of crystals, the trihydrate and the pentahydrate were several tens of microns, and the heptahydrate was several microns. The crystals precipitated are stable at a pH lower than that of the mother liquor and can be washed with water. The form of the precipitate changes with temperature; with increasing temperature, the heptahydrate changes into pentahydrate, and the pentahydrate into trihydrate. The precipitation reaction need not be conducted at an Sn/Ba ratio of 1 but can be carried out at a desired Sn/Ba ratio. It is critical to conduct the precipitation reaction in a $CO_2$-free atmosphere. In the presence of $CO_2$, $BaCO_3$ became mixed with the precipitate.

Figure 1A:
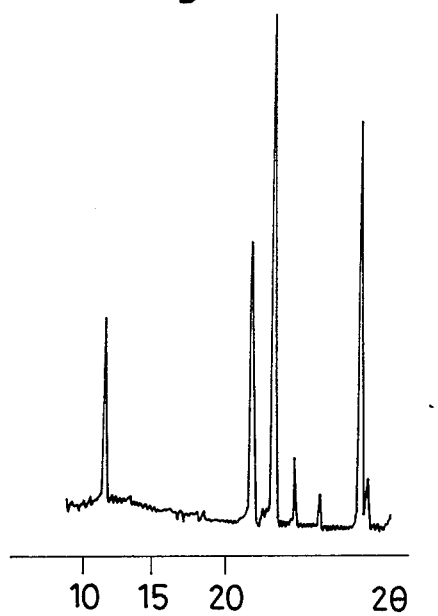
FIGS. 1a, b and c are X-ray diffraction diagrams of water-containing crystals of BaSnO$_3$, FIG. 1a being an X-ray diffraction diagram of BaSnO$_3$.3H$_2$O, FIG. 1b being an X-ray diffraction diagram of $BaSnO_3.5H_2O$ and FIG. 1c being an X-ray diffraction diagram of $BaSnO_3.7H_2O$.
Figure 1B:
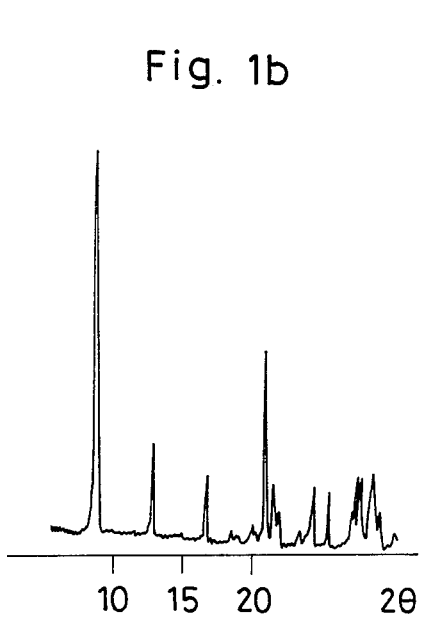
Figure 1C:
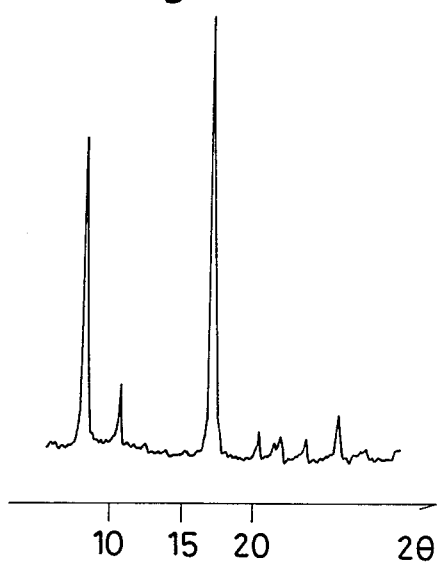

FIG. 1a shows an X-ray diffraction diagram of the trihydrate, FIG. 1b that of the pentahydrate, and FIG. 1c that of the heptahydrate. The values as to the trihydrate only are known in literature (JCPD card), which were referred to for identification.

Preferably, the reaction is conducted to form the heptahydrate or pentahydrate first, which is then washed with water and converted to the heptahydrate or trihydrate at an elevated temperature. The hydrate, when having a lower water content, is stable at a lower pH, so that the strong alkali can be removed by washing the hydrate with water. In the present example, the heptahydraten was formed first, which was washed with water and heated to obtain the pentahydrate, followed by washing with water and heating to obtain the trihydrate. The trihydrate was up to 10 ppm in alkali content. Incidentally, when the heptahydrate was washed with water only once and decomposed immediately thereafter, the product obtained was about 1000 ppmm in alkali content. Examples of solvents usable for washing are, besides water, water-methanol, water-ammonia, etc. Solvents are useful insofar as they are capable of dissolving out the alkali ion used for the preparation of water-containing crystals.

Figure 2:
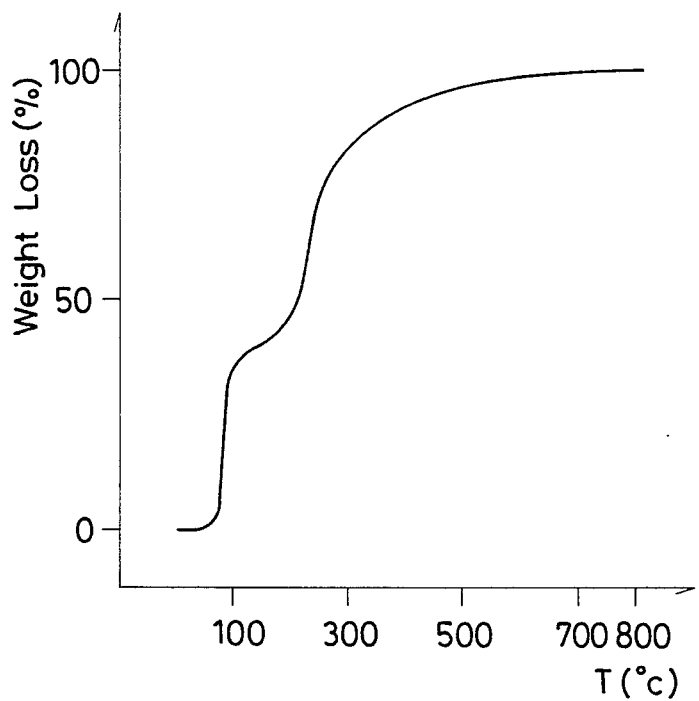
FIG. 2 is a characteristic diagram showing the result obtained by subjecting $BaSnO_3.5H_2O$ to thermogravimetric analysis.

FIG. 2 is a diagram showing the result of thermogravimetric analysis of $BaSnO_3.5H_2O$. The temperature was raised at a rate of 10° C./min. The compound was dehydrated to the trihydrate at about 100° C., and the conversion to $BaSnO_3$ occurred at about 600° C. and was completed at about 700° C. From the result thus obtained, the composition of the water-containing crystals was identified. At a lower rate of rise of temperature, the compound was completely converted to $BaSnO_3$ even at about 600° C.

The heptahydrate obtained was repeatedly washed with water and dehydrated to obtain the trihydrate via the heptahydrate. The trihydrate was then calcined at about 700° to 1500° C. to prepare $BaSnO_3$. The calcination is to be conducted in a non-reducing atmosphere such as air, oxygen or nitrogen. The $BaSnO_3$ resulting from the thermal decomposition was molded by a press, with a pair of noble metal electrodes attached to the mass of compound, followed by sintering to obtain a gas sensitive member. The molded product was sintered, for example, at a temperature of 1100° to 1500° C. in a non-reducing atmosphere, for example, for at least about 1 hour. The sintering temperature is at least 1100°

C. so that it is sufficiently higher than the temperature at which the sensor is used. The upper limit of the temperature is 1500° C. to assure ease of heating. When samples were sintered under conditions within these ranges, the resulting sensors were found almost identical in characteristics. In the following description, the sample of the present example is one prepared by thermally decomposing $BaSnO_3.3H_2O$ at 800° C. for 2 hours and sintering the product at 1400° C. in air for 2 hours. For preparing the $BaSnO_3.3H_2O$, $BaSnO_3.7H_2O$ was washed with water and heated to obtain $BaSnO_3.5H_2O$, which was then washed with water and heated and thereby converted to $BaSnO_3.3H_2O$.

The products prepared from water-containing crystals of $BaSnO_3$ via any hydrate were found free from segregated Ba or Sn because the mother crystals were perfect crystals.

Figure 3:
FIG. 3 is an electron photomicrograph showing the shape of particles obtained by thermally decomposing $BaSnO_3.3H_2O$.

One of the advantages of the present method is that the calcined product retains the original form of large acicular crystals of the hydrate and is therefore easily moldable by a press. More specifically, the product, which is particulate, is freely flowable and easily moldable into a product of high strength. FIG. 3 is an electron photomicrograph showing $BaSnO_3$ obtained by calcining $BaSnO_3.3H_2O$ at 800° C. The large acicular particles shown are skeletal particles of $BaSnO_3.3H_2O$ and are not single crystals. Crystals of $BaSnO_3.3H_2O$, when thermally decomposed, give crystals of $BaSnO_3$ which are smaller than the mother crystals. These $BaSnO_3$ crystals are interlocked with one another and retain the appearance of $BaSnO_3.3H_2O$, forming skeletal particles of $BaSnO_3.3H_2O$. $BaSnO_3.5H_2O$ or $BaSnO_3.7H_2O$, when decomposed, similarly produces skeletal particles of the mother crystals.

COMPARATIVE EXAMPLES $SnO_2$ and $BaCO_3$ were mixed together in equimolar amounts and baked in air at 1200° C. for 4 hours to obtain $BaSnO_3$. This sample was pulverized in a ball mill for 2 hours and then sintered in air at 1300° C. for 4 hours to prepare an exhaust gas sensor (Comparative Example 1-a). The sample was found to contain segregated Ba and Sn.

Another sample was similarly prepared by baking and sintering both at a temperature of 1300° C. The same pulverization and other conditions as for Comparative Example 1-a were employed. The sample obtained was also found to contain segregated Ba and Sn (Comparative Example 1-b).

The sample of Comparative Example 1-a was further pulverized in a ball mill for 2 hours, baked in air at 1300° C. for 2 hours but was still found to contain segregated elements (Comparative Example 1-c).

Figure 4:
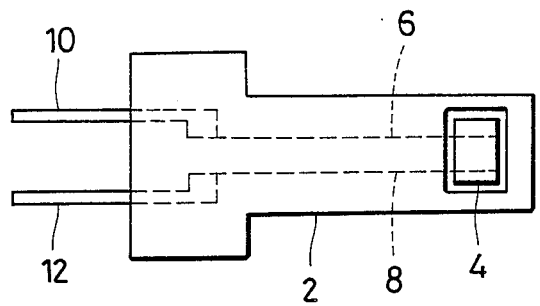
FIG. 4 is a plan view of an exhaust gas sensor embodying the invention.

$SnO_3$ and $BaCO_3$ were mixed together in equimolar amounts and reacted in air at 1300° C. for 2 hours to obtain $BaSnO_3$. This sample was repeatedly baked at 1300° C. for 2 hours and pulverized for 2 hours three times. The sample thus treated was found to be free of segregation (Comparative Example 2-a). Further $SnO_3$ and $BaCO_3$ were reacted at 1400° C. for 2 hours to obtain $BaSnO_3$, which was then repeatedly baked at 1400° C. for 2 hours and pulverized for 2 hours two times. The resulting sample was found to be free of segregation (Comparative Example 2-b). Structure of sensor FIG. 4 shows the structure of an exhaust gas sensor, which comprises an insulation substrate 2 of alumina or the like, a gas sensitive member 4 composed of $BaSnO_3$ as its active component, a pair of noble metal electrode wires 6, 8, and external leads 10, 12.

The gas sensitive member 4 was prepared by thermally decomposing $BaSnO_3.3H_2O$ at 800° C., molding the product by a press and sintering the molded piece, and is in the form of a rectangular parallelepiped measuring 2 mm × 2 mm × 0.5 mm. To utilize the skeletal particles of water-containing crystals of $BaSnO_3$, the skeletal particles obtained by the thermal decomposition were press-molded without pulverization. The pair of electrode wires 6, 8 was set in a mold conforming to the shape of the gas sensitive member 4, and skeletal particles were placed into the mold and pressed. The molded piece was then sintered in air at 1400° C. for 2 hours.

The use of skeletal particles obtained from water-containing crystals of $BaSnO_3$ by thermal decomposition facilitates the molding process. The skeletal particles of the water-containing crystals remaining after the calcination are freely flowable and can be uniformly filled into the mold. The particles serves as the skeleton of the molded piece, so that the molded piece can be obtained easily with high strength. Table 1 shows data as to the press molding operation.

TABLE 1

| Sample | Press Molding* | | |
|---|---|---|---|
| | Pressure (tons/cm$^2$) | Strength (kg/mm$^2$) | Porosity (%) |
| Prepared from $BaSnO_3.3H_2O$, sintered at 1400° C. after molding | 4 | 18 | 36 |
| Comparative Example 2-a | 4 | (not amenable to sintering because of low strength) | |
| Comparative Example 2-a sintered at 1400° C. after molding | 15 | 18 | 34 |

*Each molded piece was sintered at 1400° C. for 2 hours. The strength was measured after sintering.

The sample prepared from water-containing crystals was satisfactorily molded under a pressure of about 4 tons/cm$^2$, whereas the sample subjected to repeated pulverization and baking required a pressure of about 15 tons/cm$^2$ to obtain the same strength. The sample (Comparative Example 2-a) other than the skeletal particles was in the form of spherical particles and therefore spilled from the mold during the press-molding procedure. The sample of the present example in the form of skeletal particles did not spill from the mold.

Segregation

Figure 5A:
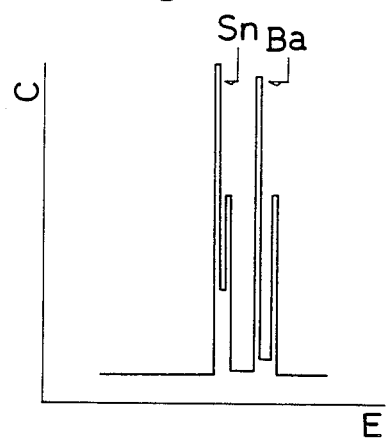
FIGS. 5a, b, c and d are X-ray spectra showing the results obtained by locally subjecting to elementary analysis to a $BaSnO_3$ crystal containing segregated elements, FIG. 5a being an X-ray spectrum of a portion where the Sn/Ba ratio is approximately 1, FIG. 5b being an X-ray spectrum of an Sn segregated portion, FIG. 5c being an X-ray spectrum of Ba segregated portion and FIG. 5d being an X-ray spectrum of the same sample as determined after actual use.
Figure 5B:
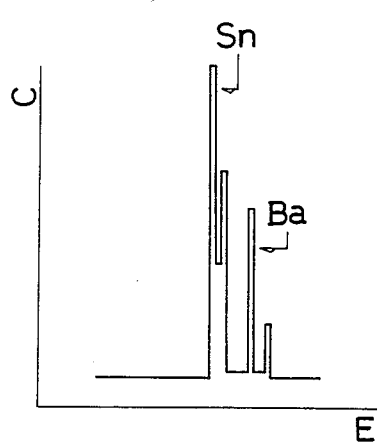
Figure 5C:
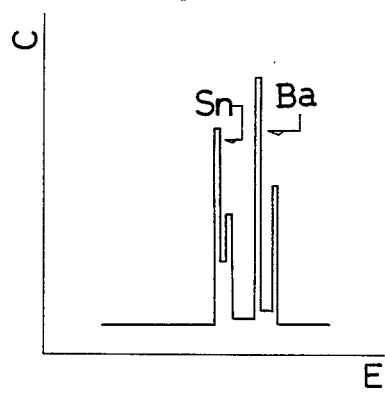
Figure 5D:
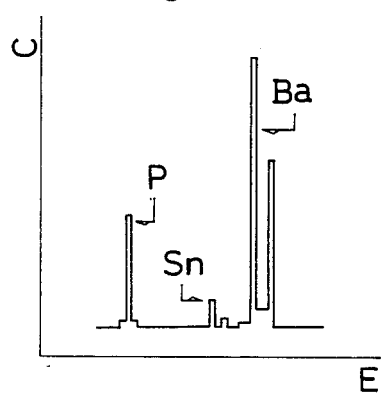

When the sample (Comparative Example 1-a) baked at 1200° C. and 1300° C. was subjected locally to X-ray elementary analysis, it was found that even one $BaSnO_3$ crystal differs in the distribution of elements from portion to portion. FIGS. 5a, b and c show the results of analysis at three positions. At the position of FIG. 5a, Sn and Ba are present uniformly. FIG. 5b shows predominant presence of Sn, whereas FIG. 5c conversely shows predominant presence of Ba. FIG. 5d shows the result obtained by analyzing the sample after exposing the sample to the exhaust gas from a motor vehicle for a total period of 8 hours. The temperature of the sensor in the exhaust gas was about 800° C., and the fuel used was usual gasoline. It is seen that Sn has disappeared with an accumulation of P, forming a compound of barium and phosphorus. However, the elementary analysis of samples free of segregation revealed a uniform Sn/Ba ratio, which remained unchanged when the sample was subjected to an exhaust gas, with only a trace of P detected. Accordingly, the segregation can be detected by local elementary analysis and is also detectable by checking the sensor for the accumulation of P after actually using the sensor in an exhaust gas. When free of segregation, $BaSnO_3$ exhibits improved durability.

The segregation is detectable also from the pH of the sample. Samples with marked segregation contain a barium-rich phase and are therefore alkaline, whereas segregation-free samples are neutral to very slightly alkaline. Even when $BaCO_3$ is admixed with $BaSnO_3$, the mixture exhibits very low alkalinity. This appears to indicate that an active barium-rich phase is present in $BaSnO_3$ with segregation and is responsible for the alkalinity. A 0.1 g quantity of $BaSnO_3$ was admixed with 1 ml of water. The mixture was allowed to stand for 1 hour, then stirred and checked for pH. The pH was 10 when the compound involved segregation, but was 8 when the compound was free of segregation.

Figure 6A:
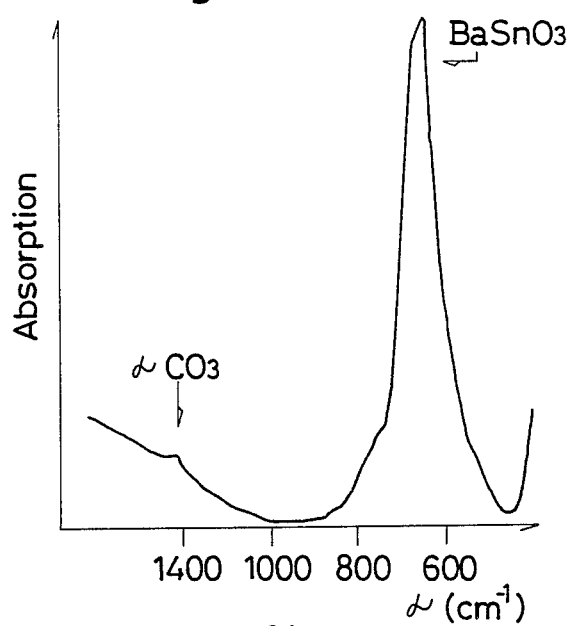
FIGS. 6a, b, c and d are Fourier transformation IR spectra of $BaSnO_3$ samples as prepared, FIG. 6a being an IR spectrum of $BaSnO_3$ containing segregated elements, FIG. 6b being an IR spectrum of $BaSnO_3$ made free of segregation by being repeatedly pulverized and baked, FIG. 6c being an IR spectrum of $BaSnO_3$ obtained by thermally decomposing $BaSnO_3.3H_2O$ and FIG. 6d being an IR spectrum of $BaSnO_3$ obtained by thermally decomposing $BaSnO_3.5H_2O$.
Figure 6B:
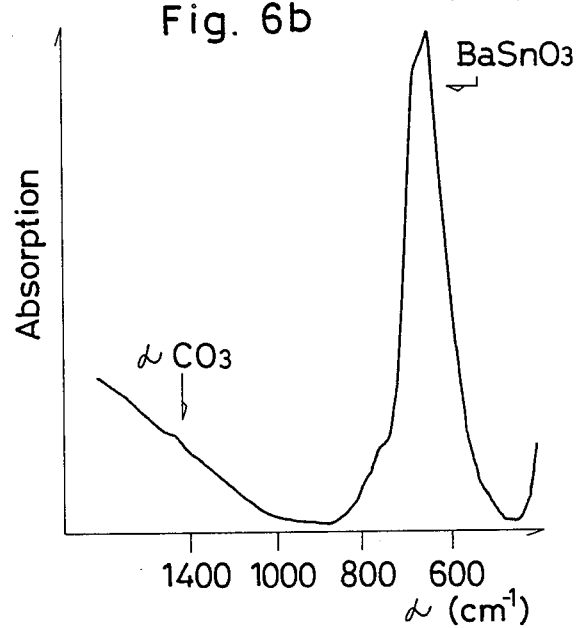
Figure 6C:
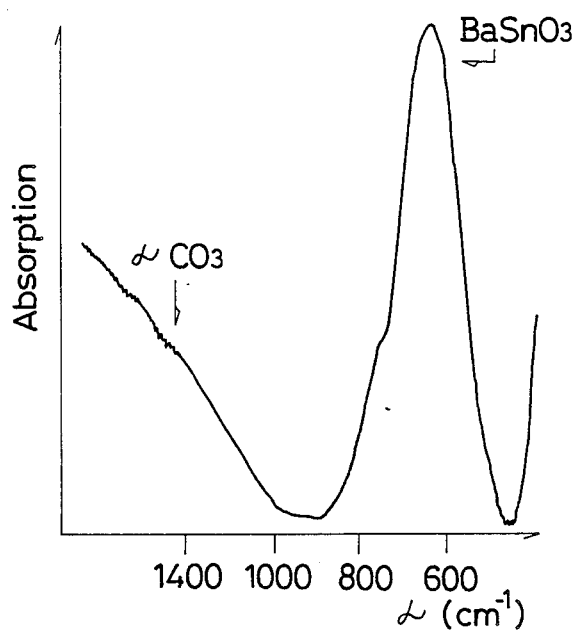
Figure 6D:
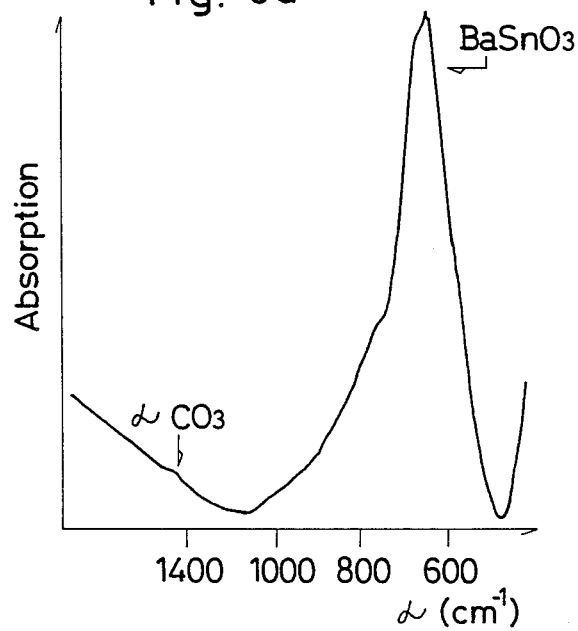

The segregation is detectable also by a highly sensitive spectroscopic method. $BaSnO_3$ was analyzed by Fourier transformation IR spectroscopy (FTIR) immediately after preparation. The segregation can be detected by checking the spectrum for the presence of a $CO_3$ ion absorption peak at about 1400 $cm^{-1}$. FIG. 6a shows an FTIR spectrum of Comparative Example 1-a, and FIG. 6b that of Comparative Example 2-a. FIG. 6c shows a spectrum of $BaSnO_3$ obtained by thermally decomposing $BaSnO_3.3H_2O$ in air at 1400° C. for 1 hour. Further FIG. 6d shows a spectrum of $BaSnO_3$ obtained by thermally decomposing $BaSnO_3.5H_2O$ in air at 1387° C. for 1 hour. A slight $CO_3$ ion absorption peak, although observable at about 1400 $cm^{-1}$, is lower than the corresponding peak of the sample (Comparative Example 1-a) with segregation. However, when samples are allowed to stand for a long period of time, e.g. for about 2 weeks, in air after preparation, the sample adsorbs $CO_2$, so that the resulting peak is sometimes difficult to distinguish from the peak due to the segregation when the above method of analysis is resorted to.

Table 2 shows the pH values of samples and the results of FTIR thereof obtained immediately after the preparation of the samples. The result of FTIR is given in the ratio of the intensity of $CO_3$ absorption to the background.

TABLE 2

| Sample | pH | FTIR |
| --- | --- | --- |
| Comparative Example 1-a | 10 | 0.2 |
| Comparative Example 1-b | 10 | 0.2 |
| Comparative Example 1-c | 10 | 0.2 |
| Comparative Example 2-a | 8 | Trace |
| Comparative Example 2-b | 8 | Trace |
| From $BaSnO_3.3H_2O$ | 8 | Trace |
| From $BaSnO_3.5H_2O$ | 8 | Trace |
| From $BaSnO_3.7H_2O$ | 8 | Trace |

Durability in actual use

Sensors incorporating $BaSnO_3$ with segregation exhibit increased resistance and decreased oxygen sensitivity during actual use.

The sensor was tested under the conditions of actual use as installed in the exhaust pipe of a motor vehicle engine, by operating the engine at an air-fuel ratio (A/F) of 20 for 1 hour once a day. The sensor was held at a temperature of about 800° C. during the operation of the engine and allowed to stand at room temperature while it was out of operation. The sensor was incorporated into a bridge circuit, which was adapted to produce an output of 0 at a point slightly toward the lean side from the point of equivalence, by adjusting the bridge resistors. The output becomes positive with a change toward the lean side or negative with a change toward the rich side.

Figure 7:
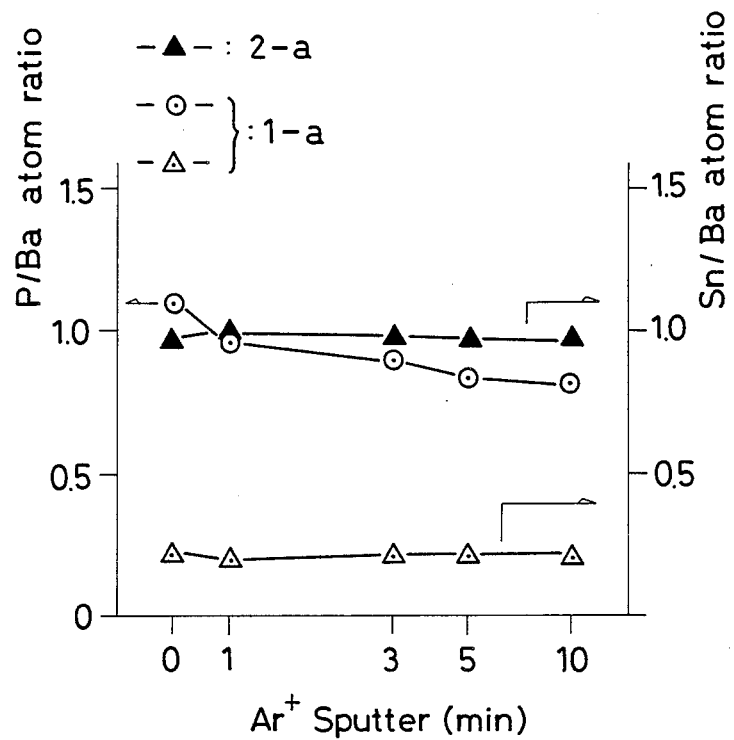
FIG. 7 is an elementary analysis diagram showing the decomposition due to actual use of $BaSnO_3$ containing segregated elements.

The surface of the sensor of Comparative Example 1-a was etched by Ar ion puttering after actual use and checked for composition depthwise from the surface. FIG. 7 shows the result, revealing a reduction in Sn concentration and an accumulation of P due to the exhaust gas. Nevertheless, the segregation-free sensor was found to contain no P and to be constant in Sn/Ba ratio. Although FIG. 7 shows the data obtained with Comparative Example 2-a as an example of segregation-free sample, the same result was achieved with use of the sample from water-containing crystals of $BaSnO_3$. This indicates that the segregation triggers decomposition of $BaSnO_3$ with the exhaust gas. The above result corresponds to the result of FIG. 5d.

Figure 8:
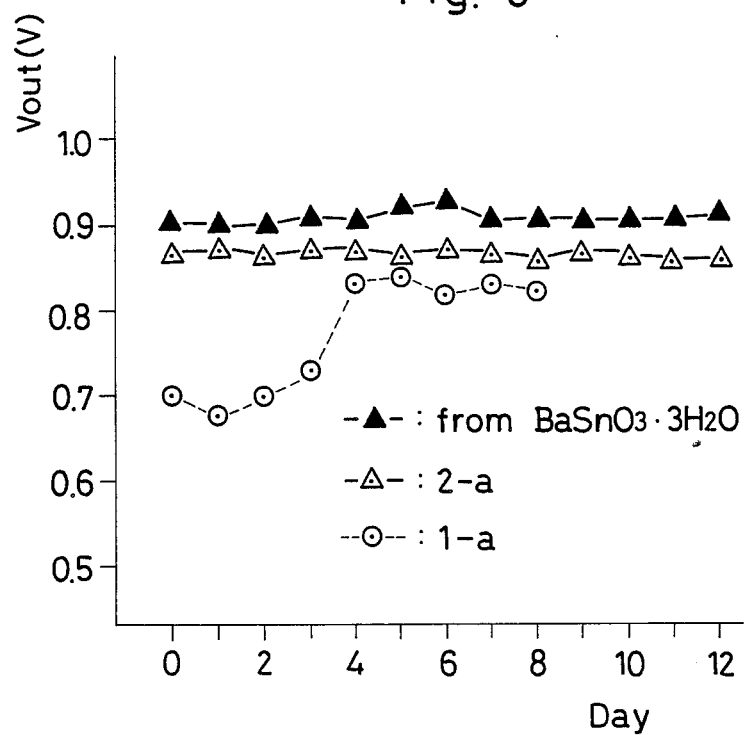
FIG. 8 is a characteristics diagrams showing the relation between segregation in $BaSnO_3$ and durability as determined with lapse of time.

FIG. 8 shows the output characteristics of the samples of Comparative Example 1-a (broken line), Comparative Example 2-a and the present example prepared from $BaSnO_3$ trihydrate, as determined by actual use. In the case of the sample with segregation (Comparative Example 1-a), the sensor exhibits resistance which increases with time and produces an unstable output.

Table 3 shows variations in the characteristics as determined by actual use for 8 days.

TABLE 3

| Sample | Durability* Resistance ratio | Variation in oxygen gradient |
| --- | --- | --- |
| Comparative Example 1-a | 1.4 | 0.20 → 0.18 |
| Comparative Example 2-a | 1.0 | 0.24 → 0.24 |
| Comparative Example 2-b | 1.0 | 0.23 → 0.23 |
| Thermally decomposed trihydrate | 1.0 | 0.25 → 0.24 |

*The resistance ratio is the ratio of the resistance after 8 days to the initial resistance. The oxygen gradient is given by m in the equation of log Rs = K + m.log Po$_2$ wherein Rs is the sensor resistance, and K is a constant. Each value was measured at a temperature of 800° C. and was the average of three sensors.

The sensors incorporating segregation-free $BaSnO_3$ are stabilized in resistance and oxygen sensitivity and exhibit improved oxygen sensitivity.

Other characteristics

The segregation affects other characteristics of the sensor. For example, when exposed to a highly oxidizing atmosphere or strongly reducing atmosphere, the sensor undergoes variations in resistance and in the speed of response. When the sensor is exposed to a poisoning substance such as $SO_2$, the resistance also varies. Elimination of the segregation gives the sensor improved durability against these atmospheres and poisons.

Figure 9:
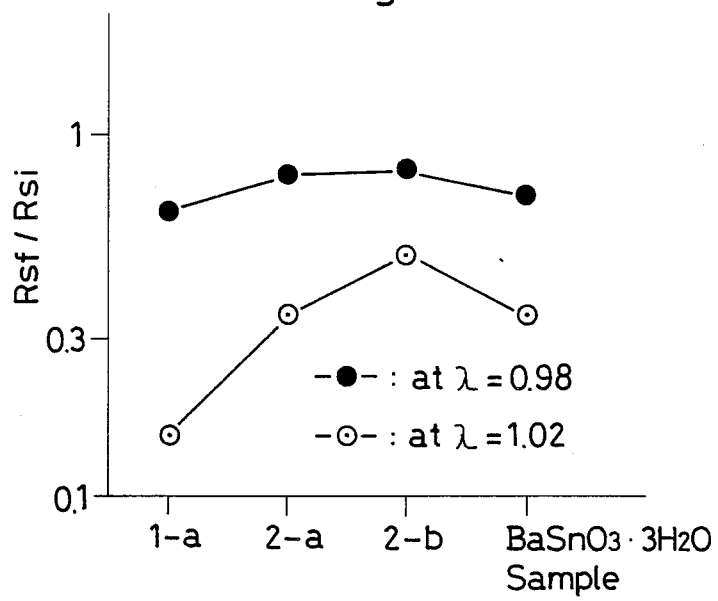
FIG. 9 is a characteristics diagram showing variations in the resistance value of exhaust gas sensors during use under severe conditions.

Sensors were tested for durability against a strongly oxidizing atmosphere and strongly reducing atmosphere by the following method. The sensor was held for 14 days in an atmosphere maintained at 900° C. while varying the equivalent ratio λ between 1.1 and 0.9 at a time interval of 10 minutes. The variation in the resistance value resulting from the test was determined at λ values of 1.02 and 0.98 at 700° C. Also determined was the variation in the response speed between the oxidation side and the reduction side at 700° C. The results are given in FIGS. 9 and 10. FIG. 9 shows the ratio of the resistance value after testing to that before testing. The sample with segregation (Comparative Example 1-a) exhibited a great reduction in resistance at the oxidation side.

Figure 10:
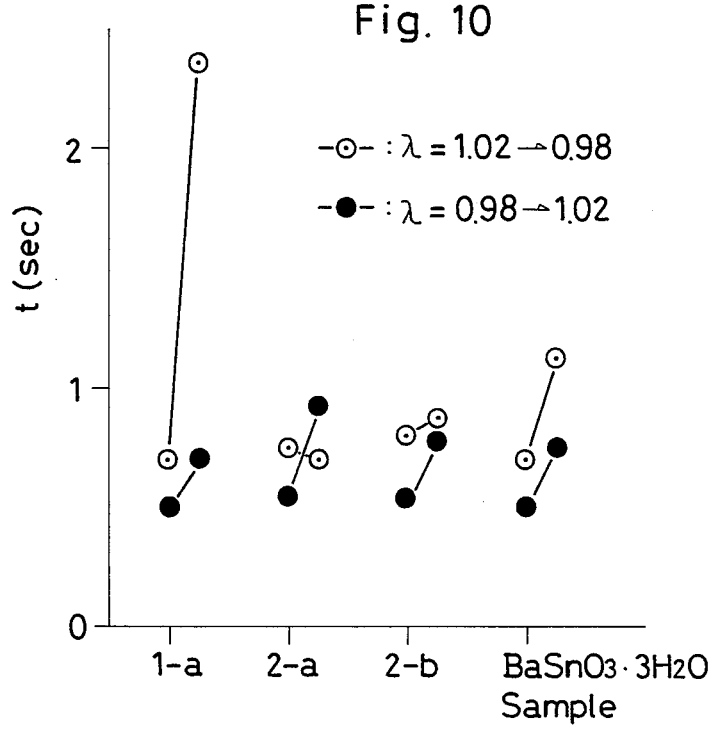
FIG. 10 is a characteristics diagram showing variations in the speed of response of exhaust gas sensors during use under severe conditions.

FIG. 10 shows the variation in the response time as determined by the testing. The response time is expressed in terms of response time for a change of λ between 0.98 and 1.02 at 700° C. and is the time required from 10% response to 90% response. The decrease in the response speed can be prevented by eliminating the segregation.

Figure 11:
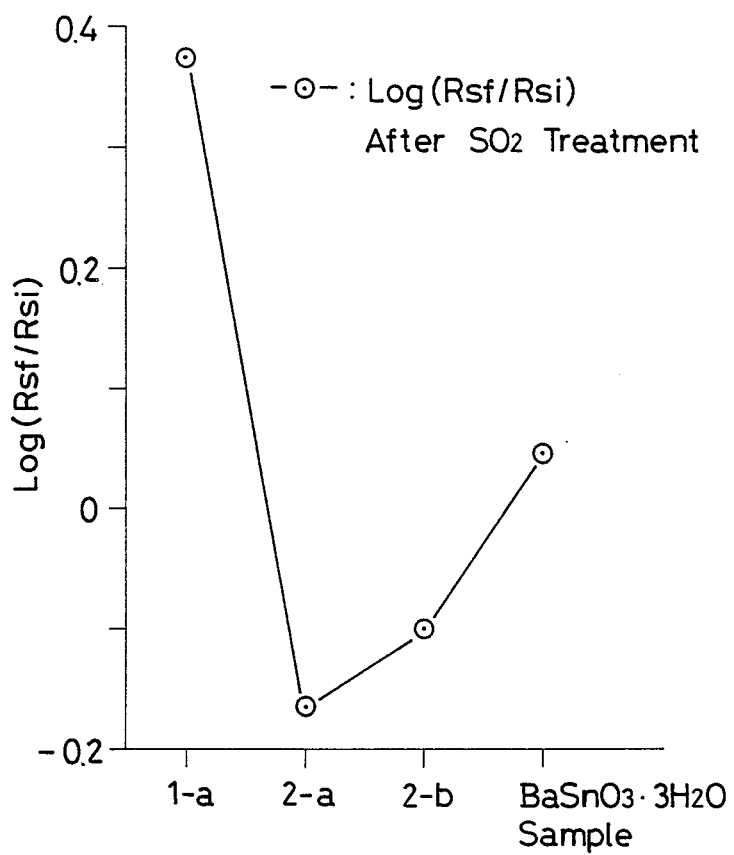
FIG. 11 is a characteristics diagram showing resistance to $SO_2$ poisoning.

The sensor was heated at 700° C. in a $N_2$-balanced system of 5.5% $O_2$ containing 20 torr of water vapor, and the resistance was measured. Subsequently, the sensor was cooled to room temperature and exposed to 500 ppm of $SO_2$ for 3 hours for poisoning. The sensor was thereafter heated to 700° C. and checked for resistance to determine the resulting variation. FIG. 11 shows the result. It is seen that the sensor has improved resistance to poisoning with $SO_2$ when free of the segregation.

Supplement

Although $BaSnO_3.3H_2O$ was thermally decomposed to obtain $BaSnO_3$ having a high purity according to the present example, $BaSnO_3.5H_2O$, $BaSnO_3.7H_2O$ or the like may be thermally decomposed into $BaSnO_3$. Further the exhaust gas sensor may be shaped or constructed as desired. Suitable additives may be incorporated into $BaSnO_3$, or some component of $BaSnO_3$ may be replaced by other element.

What is claimed is:

1. A method of increasing the durability and oxygen sensitivity of an exhaust gas sensor having a $BaSnO_3$ gas sensitive member by the thermal decomposition of water-containing crystals of $BaSnO_3$ and employing the $BaSnO_3$ so prepared in an exhaust gas sensor including the $BaSnO_3$ gas sensitive member, an insulating substrate and external leads.

2. Method of claim 1, wherein the thermal decomposition is conducted at a temperature of at least about 600° C.

3. Method of claim 2, including the further step of sintering the product of the thermal decomposition step.

4. Method od claim 3, wherein the sintering is conducted at a temperature of about 1100° C. to about 1500° C.

5. A method as defined in claim 1 wherein the water-containing crystals of $BaSnO_3$ are prepared by subjecting stannate ion and barium ion to a precipitation reaction in a strongly alkaline solution.

6. A method as defined in claim 5 wherein the precipitation reaction is conducted in the absence of $CO_2$.

7. A method as defined in claim 1 wherein the water-containing crystals of $BaSnO_3$ are crystals of at least one member selected from the group consisting of $BaSnO_3.3H_2O$, $BaSnO_3.5H_2O$ and $BaSnO_3.7H_2O$.

8. A method as defined in claim 7 wherein crystals of at least one member selected from the group consisting of $BaSnO_3.5H_2O$ and $BaSnO_3.7H_2O$ are washed with heating to prepare crystals of $BaSnO_33H_2O$, and the crystals prepared are thermally decomposed into $BaSnO_3$.

9. A method as defined in claim 7 wherein the water-containing crystals of $BaSnO_3$ are thermally decomposed to obtain skeletal particles, and the particles are molded by a press without pulverization and thereafter sintered.

* * * * *